US008067206B2

(12) United States Patent
Engel et al.

(10) Patent No.: US 8,067,206 B2
(45) Date of Patent: Nov. 29, 2011

(54) ENHANCED COAMPLIFICATION OF NUCLEIC ACIDS

(75) Inventors: Holger Engel, Hilden (DE); Dirk Löffert, Düsseldorf (DE)

(73) Assignee: Qiagen GmbH, Hilden (DE)

( * ) Notice: Subject to any disclaimer, the term of this patent is extended or adjusted under 35 U.S.C. 154(b) by 731 days.

(21) Appl. No.: 10/669,976

(22) Filed: Sep. 24, 2003

(65) Prior Publication Data

US 2004/0115712 A1 Jun. 17, 2004

(30) Foreign Application Priority Data

Sep. 24, 2002 (EP) .................................... 02021174

(51) Int. Cl.
*C12Q 1/68* (2006.01)
*C12N 15/09* (2006.01)
(52) U.S. Cl. ...................................................... 435/91.2
(58) Field of Classification Search .................. None
See application file for complete search history.

(56) References Cited

U.S. PATENT DOCUMENTS

| 4,683,195 | A | | 7/1987 | Mullis et al. | |
|---|---|---|---|---|---|
| 4,683,202 | A | | 7/1987 | Mullis | |
| 4,740,594 | A | * | 4/1988 | Mauzac et al. | 536/51 |
| 4,902,624 | A | | 2/1990 | Columbus et al. | |
| 4,965,188 | A | | 10/1990 | Mullis et al. | |
| 5,106,730 | A | | 4/1992 | Van Ness et al. | |
| 5,173,260 | A | | 12/1992 | Zander et al. | |
| 5,185,243 | A | | 2/1993 | Ullman et al. | |
| 5,194,370 | A | | 3/1993 | Berninger et al. | |
| 5,229,297 | A | | 7/1993 | Schnipelsky et al. | |
| 5,411,876 | A | | 5/1995 | Bloch et al. | |
| 5,459,038 | A | * | 10/1995 | Reed et al. | 435/6 |
| 5,705,366 | A | * | 1/1998 | Backus | 435/91.2 |
| 5,773,258 | A | * | 6/1998 | Birch et al. | 435/91.2 |
| 6,183,998 | B1 | | 2/2001 | Ivanov et al. | |

FOREIGN PATENT DOCUMENTS

EP A-0 402 994 11/1994

OTHER PUBLICATIONS

Bustin SA "Absolute Quantification of mRNA using real-time reverse transcription polymerase chain reaction assays", Journal of Molecular Endocrinology, 2000, vol. 25, p. 169-193.*
Lantz P et al. "Removal of PCR inhibitors from human faecal samples through the use of an aqeous two-phase system for sample preparation prior to PCR", Journal of Microbiological Methods, 1997, vol. 28, p. 159-167.*
Dextran 40, JBC Handbook, 4th edition, 1997, 2 pages.*
Bustin SA "Absolute Quantification of mRNA using real-time reverse transcription polymerase chain reaction assays", Journal of Molecular Endocrinology, 2000, vol. 25, p. 169-193.*
Mansfield et al. (Molecular Cellular Probes, 1995, vol. 9, p. 145-156).*
Mansfield et al. (Molecular Cellular Probes, 1995, vol. 9, p. 145-156).*
Grondahl et al. (J. Clin. Micro., 1999, 37(1):1-7).*
Henegariu et al. (Biotechniques, 1997, vol. 23, p. 504-511).*
Bustin, S.A., *J. Mol. Endocrinol.*, 25, 169-193 (2000).
Chou et al., *Nucleic Acids Research* 20(7): 1717-1723 (1992).
Freeman, W.M. et al., *Biotechniques*, 26, 112-125 (1999).
Markoulatos et al., Journal of Clinical Laboratory Analysis 16:47-51 (2002).
Karge et al., Methods in Molecular Biology, vol. 110 Lipoprotein Protocols, Edited by J M Ordovas, Humana Press Inc , Totowa, NJ, pp. 43-61, 1998.
User Bulletin #5, ABI PRISM® 7700 Sequence Detection System, Aug. 10, 1998 (updated Jan. 2001).

* cited by examiner

*Primary Examiner* — Stephanie K Mummert
(74) *Attorney, Agent, or Firm* — Fanelli Haag PLLC (57) ABSTRACT

The present invention relates generally to the field of nucleic acid chemistry. More specifically, it relates to a method for enhancing the performance of coamplification reactions, e.g., multiplex PCR reactions.

28 Claims, 2 Drawing Sheets

SEQUENCE LISTING

<160> NUMBER OF SEQ ID NOS: 22

<210> SEQ ID NO 1
<211> LENGTH: 23
<212> TYPE: DNA
<213> ORGANISM: artificial
<220> FEATURE:
<223> OTHER INFORMATION: primer

<400> SEQUENCE: 1
gctgcttgaa gaaacgagcg gtg                                        23

<210> SEQ ID NO 2
<211> LENGTH: 24
<212> TYPE: DNA
<213> ORGANISM: artificial
<220> FEATURE:
<223> OTHER INFORMATION: primer

<400> SEQUENCE: 2
ctgcaccttc tggaattccg actc                                       24

<210> SEQ ID NO 3
<211> LENGTH: 25
<212> TYPE: DNA
<213> ORGANISM: artificial
<220> FEATURE:
<223> OTHER INFORMATION: primer

<400> SEQUENCE: 3
atgtggtccc tgtggaagat aacga                                      25

<210> SEQ ID NO 4
<211> LENGTH: 25
<212> TYPE: DNA
<213> ORGANISM: artificial
<220> FEATURE:
<223> OTHER INFORMATION: primer

```
<400> SEQUENCE: 4
gcgacatgtg ctttgaggaa ctgtt                                    25

<210> SEQ ID NO 5
<211> LENGTH: 30
<212> TYPE: DNA
<213> ORGANISM: artificial
<220> FEATURE:
<223> OTHER INFORMATION: primer

<400> SEQUENCE: 5
atcctccttc tatagtctgt ccaagagtag                               30

<210> SEQ ID NO 6
<211> LENGTH: 28
<212> TYPE: DNA
<213> ORGANISM: artificial
<220> FEATURE:
<223> OTHER INFORMATION: primer

<400> SEQUENCE: 6
cctccagaaa aagctagata ctaacctt                                 28

<210> SEQ ID NO 7
<211> LENGTH: 22
<212> TYPE: DNA
<213> ORGANISM: artificial
<220> FEATURE:
<223> OTHER INFORMATION: primer

<400> SEQUENCE: 7
atcaggtgcg aatgttcgct cg                                       22

<210> SEQ ID NO 8
<211> LENGTH: 22
<212> TYPE: DNA
<213> ORGANISM: artificial
<220> FEATURE:
<223> OTHER INFORMATION: primer

<400> SEQUENCE: 8
ctcgctgcag tcgcggttgg ag                                       22

<210> SEQ ID NO 9
<211> LENGTH: 21
<212> TYPE: DNA
<213> ORGANISM: artificial
<220> FEATURE:
<223> OTHER INFORMATION: primer

<400> SEQUENCE: 9
ttgggtttgc aggaattgga a                                        21

<210> SEQ ID NO 10
<211> LENGTH: 26
<212> TYPE: DNA
<213> ORGANISM: artificial
<220> FEATURE:
<223> OTHER INFORMATION: primer

<400> SEQUENCE: 10
gtttctaagg cacccattcg atacac                                   26

<210> SEQ ID NO 11
<211> LENGTH: 24
```

```
<212> TYPE: DNA
<213> ORGANISM: artificial
<220> FEATURE:
<223> OTHER INFORMATION: primer

<400> SEQUENCE: 11
cgcctgtgca gtggtgagtc agtg                                          24

<210> SEQ ID NO 12
<211> LENGTH: 24
<212> TYPE: DNA
<213> ORGANISM: artificial
<220> FEATURE:
<223> OTHER INFORMATION: primer

<400> SEQUENCE: 12
actggattga acctcggagg gtcg                                          24

<210> SEQ ID NO 13
<211> LENGTH: 25
<212> TYPE: DNA
<213> ORGANISM: artificial
<220> FEATURE:
<223> OTHER INFORMATION: primer

<400> SEQUENCE: 13
acagtgaacg tggaggatag tggtg                                         25

<210> SEQ ID NO 14
<211> LENGTH: 24
<212> TYPE: DNA
<213> ORGANISM: artificial
<220> FEATURE:
<223> OTHER INFORMATION: primer

<400> SEQUENCE: 14
cccaaggctt aggctcagta gtga                                          24

<210> SEQ ID NO 15
<211> LENGTH: 26
<212> TYPE: DNA
<213> ORGANISM: artificial
<220> FEATURE:
<223> OTHER INFORMATION: primer

<400> SEQUENCE: 15
agattatgga cttccagccc gtacac                                        26

<210> SEQ ID NO 16
<211> LENGTH: 25
<212> TYPE: DNA
<213> ORGANISM: artificial
<220> FEATURE:
<223> OTHER INFORMATION: primer

<400> SEQUENCE: 16
gtacccagta ccggcagaga ctcac                                         25

<210> SEQ ID NO 17
<211> LENGTH: 32
<212> TYPE: DNA
<213> ORGANISM: artificial
<220> FEATURE:
<223> OTHER INFORMATION: primer

<400> SEQUENCE: 17
ttctgtttat atctttattt tttaatcacc cc                                 32
```

```
<210> SEQ ID NO 18
<211> LENGTH: 31
<212> TYPE: DNA
<213> ORGANISM: artificial
<220> FEATURE:
<223> OTHER INFORMATION: primer

<400> SEQUENCE: 18
agaaagctaa gcatttatct caagaaaata g                                           31

<210> SEQ ID NO 19
<211> LENGTH: 32
<212> TYPE: DNA
<213> ORGANISM: artificial
<220> FEATURE:
<223> OTHER INFORMATION: primer

<400> SEQUENCE: 19
aaattctctg ggttttggtc tgttgtgctt tt                                          32

<210> SEQ ID NO 20
<211> LENGTH: 20
<212> TYPE: DNA
<213> ORGANISM: artificial
<220> FEATURE:
<223> OTHER INFORMATION: primer

<400> SEQUENCE: 20
ccctattcgc tccggatctc                                                        20

<210> SEQ ID NO 21
<211> LENGTH: 18
<212> TYPE: DNA
<213> ORGANISM: artificial
<220> FEATURE:
<223> OTHER INFORMATION: primer

<400> SEQUENCE: 21
gccggctagg gtggaaga                                                          18

<210> SEQ ID NO 22
<211> LENGTH: 18
<212> TYPE: DNA
<213> ORGANISM: artificial
<220> FEATURE:
<223> OTHER INFORMATION: primer

<400> SEQUENCE: 22
acgcccgcag cgcagctc                                                          18
```

ENHANCED COAMPLIFICATION OF NUCLEIC ACIDS

This application claims priority under 35 U.S.C. §119(a) and (b) to European Application No. 02021174.4, filed Sep. 24, 2002.

FIELD OF THE INVENTION

This invention relates generally to the field of nucleic acid chemistry. More specifically, it relates to a method for enhancing the performance of coamplification reactions, e.g. multiplex PCR reactions.

BACKGROUND OF THE INVENTION

Detection of nucleic acids has grown in recent years as a means for early detection of genomic features, infectious agents and various organisms which are present in very small quantities in a human, plant, microbial or animal test specimen. Detection procedures are normally based on the concept of complementarity whereby two DNA strands are bound together by hydrogen bonds and other forces between complementary nucleotides (which are known as nucleotide pairs).

A DNA molecule is normally quite stable, but the strands can be separated or denatured by certain conditions, such as heating. The denatured strands will reassociate only with another strand having a complementary sequence of nucleotides.

Much research has been carried out to find ways to detect only a few molecules of a DNA. Various procedures are known and have been used for more than a decade to amplify or greatly multiply the number of nucleic acids in a specimen for detection. Such amplification techniques include polymerase chain reaction (PCR), ligase chain reaction (LCR) and others which are less developed.

Both chain reactions—in particular the polymerase chain reaction (PCR) process—for amplifying nucleic acid sequences are well known in the art and disclosed in U.S. Pat. Nos. 4,683,202; 4,683,195; and 4,965,188.

In each cycle of a PCR amplification, a double-stranded target sequence is denatured, primers are annealed to each strand of the denatured target, and the primers are extended by the action of a DNA polymerase. Specificity of amplification depends on the specificity of primer hybridisation, also referred to primer annealing. Primers are selected to be complementary to, or substantially complementary to, sequences occurring at the 3' end of each strand of the target nucleic acid sequence. Under the elevated temperatures used in a typical PCR, the primers hybridize only to the intended target sequence. However, amplification reaction mixtures are typically assembled at room temperature, well below the temperature needed to ensure primer hybridization specificity. Under such less stringent conditions, the primers may bind non-specifically to other only partially complementary nucleic acid sequences (or even to other primers) and initiate the synthesis of undesired extension products, which can be amplified along with the target sequence. Amplification of the non-specific primer extension products can compete with amplification of the desired target sequences and can significantly decrease the efficiency of the amplification of the desired sequence. Problems caused by non-specific amplification are discussed further in Chou et al., 1992, Nucleic Acids Research 20(7):1717-1723, incorporated herein by reference.

Non-specific amplification can be reduced by reducing the formation of extension products from primers bound to non-complementary target sequences prior to the start of the reaction. In one method, referred to as a "hot-start" protocol, one or more critical reagents are withheld from the reaction mixture until the temperature is raised sufficiently to provide the necessary hybridization specificity. In this manner, the reaction mixture cannot support primer extension during the time that the reaction conditions do not ensure specific primer hybridization.

Hot-start methods can be carried out manually by opening the reaction tube after the initial high temperature incubation step and adding the missing reagents. However, manual hot-start methods are labor intensive and increase the risk of contamination of the reaction mixture. Hot-start methods which use a heat labile material, such as wax, to separate or sequester reaction components are described in U.S. Pat. No. 5,411,876, incorporated herein by reference, and Chou et al., 1992, supra. In these methods, a high temperature pre-reaction incubation melts the heat labile material, thereby allowing the reagents to mix.

Methods and reagents for amplifying nucleic acid using a primer-based amplification reaction which provide a simple and economical solution to the problem of non-specific amplification are known from the state of the art (e.g. U.S. Pat. Nos. 5,773,258 or 6,183,998). The methods use a reversibly inactivated thermostable enzyme which can be reactivated by incubation in the amplification reaction mixture at an elevated temperature. Non-specific amplification is greatly reduced because the reaction mixture does not support primer extension until the temperature of the reaction mixture has been elevated to a temperature which insures primer hybridization specificity.

Another problem does arise from the fact that human and animal specimens contain many different nucleic acids, some of which are endogenous (or natural) to the person or animal, and others which are produced because of some abnormal condition, such as from the presence of an infectious agent or an oncogenic condition. Such nucleic acids are usually present in very low concentrations compared to endogenous nucleic acids. They are sometimes referred to as "low copy number" nucleic acids. By comparison, the endogenous nucleic acids are usually present in high concentrations and may be referred to as "high copy number" nucleic acids. One such example is human β-globin DNA. Frequently, in using PCR, two or more nucleic acids present in the specimen are amplified at the same time in the same reaction container. This is identified herein as "co-amplification". This process requires that primers for each nucleic acid to be amplified must be simultaneously present in the container.

When both low and high copy target nucleic acids are amplified in such situations, amplification of the low copy target nucleic acid is often inhibited. This is due to the saturation of the amplifying enzyme (such as DNA polymerase) by the high copy target nucleic acid during the later cycles of amplification. False negative results for the presence of the low copy target nucleic acid are likely, with possibly serious consequences.

A similar problem arises if such co-amplification reactions shall be carried out for quantitative measurements of nucleic acid molecules such as quantitative PCR. Quantitative PCR and quantitative reverse transcription-polymerase chain reaction (RT-PCR) is used for determining the amount of specific DNA or RNA molecules in biological samples. The method has evolved from a low-throughput gel-based analysis to the use of fluorescence techniques that do not require the separation of the reaction product on a gel ('closed tube' format).

The amount of DNA or cDNA amplified by a PCR is then proportional to an increase in the fluorescent signal. The amount of starting DNA is then determined by analyzing the fluorescence at each cycle of PCR (real-time or online PCR), or after the PCR (end-point detection). These fluorescent techniques which most often comprise fluorescent labelled sequence-specific probes are faster and can be less expensive since they do not require post-PCR. These methods also reduce contamination of the laboratory with PCR amplicon molecules that may interfere with subsequent assays. Background on quantitative PCR and quantitative real-time PCR is given in: Freeman, W. M. et al., 1999, Biotechniques, 26, 112-125 and Bustin, S. A., 2000, J. Mol. Endocrinol., 25, 169-193). Most methods rely on the use of an oligonucleotide labelled with a fluorophore and a quencher moiety. The quencher reduces the fluorescence of the fluorophore by fluorescence resonance energy transfer (FRET) when the two moieties are separated by <100 Å (Clegg, R. M., 1992, Methods Enzymol., 211, 353-388). During PCR, the fluorophore and quencher are separated in space causing an increase in fluorescence. The separation occurs either by cleavage of the oligonucleotide also referred to as 5'-3' exonuclease assay, or by a change in secondary structure of the oligonucleotide probe when it anneals to target DNA, as occurs with molecular beacons or scorpion primers (For a recent, although not complete, review on recent probe technologies see Didenko, V. D., 2001, Biotechniques, 31: 1106-1121). Quantitative, real-time, multiplex PCR with two sets of differently labeled gene-specific probes is useful because one primer/probe set may be used to detect the amount of a gene that is variable and another to detect a gene that is relatively constant and is used as a reference for the quantification of the variable gene. When both, the low and high copy target nucleic acids are amplified in one reaction, amplification of the low copy target nucleic acid is often interfered by the amplification of the high copy target gene due to the saturation of the amplifying enzyme (such as DNA polymerase) by the high copy target nucleic acid during the later cycles of amplification. Therefore, failure of quantification or inaccurate quantification is often the result of such assays making comparison between different nucleic acid samples difficult. This can dramatically affect the interpretation of experimental or clinical results such as the wrong estimation of the viral load in the blood of a patient undergoing therapy.

However, co-amplification reactions do not only possess a problem for reactions in which the nucleic acids to be amplified exist at varying copy numbers such as in quantitative PCR or RT-PCR. Simultaneous amplification of nucleic acid molecules which are contained in a nucleic acid sample is often compromised by competition of the various amplification products for limiting reaction parameters. Such applications comprise e.g. the co-amplification of genetic markers for determining genomic variabilities such as short tandem repeats (STRs), variable number tandem repeats (VNTRs) or single nucleotide polymorphisms (SNPs). The determination of these genomic variabilities are increasingly used in research and diagnostic applications such as drug discovery, pharmacology, patient management, population genetics, genotyping e.g. for paternity testing, forensics, pathology and breeding analysis.

Various solutions to this problem have been proposed for PCR, including adjusting the concentrations of the primers, use of different polymerase amounts, specialised reaction buffer formulations or utilizing primer sets with specific melting temperatures ($T_m$'s), or combinations thereof. Adjusting the primer ratios has been referred in the art as "primer biasing" the PCR yield, and requires a decrease in the concentration of primers for the high copy target nucleic acid or of the nucleic acid molecule which is preferentially amplified. Only modest control of the process is achieved with this approach.

Another approach to co-amplification has been to adjust the temperature of annealing in PCR such that the primers for the high copy target nucleic acid or the preferentially amplified nucleic acid anneal to a lesser extent than those for the low copy target nucleic acid or the inefficient amplified nucleic acid. This approach also has a problem. The $T_m$ difference between primer pairs must be relatively large before good modulation of PCR can be exerted on the differential yields for the high and low copy nucleic acids. Exact $T_m$'s cannot be calculated (although they can be estimated), and thus they must be measured. This requires a high degree of effort, and are considerably tedious.

Alternatively, adding time to the priming or extension steps in PCR in all cycles can minimize the DNA polymerase saturation by the high copy target nucleic acid or the more efficiently amplified nucleic acid and increase amplification efficiency. However, this solution has limited utility in situations where many nucleic acids which are present in varying concentrations, are being amplified simultaneously or if amplification products differ significantly in size.

It is known that the hybridization rate of nucleic acids is increased considerably in the presence of volume exclusion agents such as dextran sulfate or polyethylene glycol due to exclusion of nucleic acids from the volume of solution occupied by the agents "Sambrook et al, Molecular Cloning, A Laboratory Manual", page 9.50, 1989, and U.S. Pat. No. 5,106,730 (Van Ness et al.). This exclusion effect increases the effective concentration of the nucleic acids in the solution, thereby increasing the rate of hybridization. Thus, such materials are routinely added to reaction mixtures to "drive" unfavourable reactions forward. For example, they are added to reaction mixtures to "drive" ligase reactions, U.S. Pat. No. 5,185,243 (Ullman et al.) and U.S. Pat. No. 5,194,370 (Berninger et al.).

All patents, patent applications, and publications mentioned herein, both supra and infra, are incorporated herein by reference.

The Problem Underlying the Present Invention

As mentioned above, in multiplex PCR reactions, many different primers are present that may bind non-specifically to the template nucleic acid. This is due to the fact that PCR reactions are typically assembled at room temperature, much below the temperature that ensures specific hybridisation of the primers. Such non-specific extension of primers decreases the performance and sensitivity of the assay, because unwanted reactions, caused by primers bound and extended non-specifically, dramatically decrease the efficiency of the reaction.

In addition, due to the presence of many different primers in the reaction, the probability that at least some of these primers even interact with each other is high. Typically, the products of such interactions are referred to as primer dimers. Presence of primer dimers dramatically reduces the efficiency of the reaction.

Efficient co-amplification of multiple targets (multiplex PCR) is only possible when reaction conditions are chosen that allow all reactions to take place simultaneously and all reactions only minimally influence each other. This is only possible when the plateau phase of each reaction is limited. Limited height of PCR plateaus can be achieved by limiting the concentration of PCR primers. However, limited concentrations of primers may result in decreased sensitivity of the PCR assay.

Some of the effects described above can be eliminated by the use of a PCR hot start technique described above. However, in co-amplification reactions (multiplex reactions) using equimolar concentrations of all primers it is frequently observed that the yield of some amplification products is much lower than from others. Some amplification products may even not be detectable at all, even when a comparable number of copies of the target DNA sequence are present within the reaction. This may be even more pronounced when low concentrations of primers are used, which is required to minimize the influence of the reactions on each other. Strong differences in product yield are due to differences in hybridisation of the primers to their respective target sequence and extension of such annealed primers. When such differences in product yield are observed, researchers typically need to adapt the concentration of primers to obtain comparable product yield. Establishment of the optimal molar ratio of primers is typically very difficult to perform.

The hybridisation of primers in each cycle of PCR can be increased by a dramatically prolonged annealing step in each PCR cycle. This dramatically increases the overall time for an multiplex PCR assay, which decreases convenience and is unwanted or not acceptable in most cases.

Accordingly, it would be desirable to achieve rapid and efficient amplification of one or more target nucleic acids when co-amplified in the presence of one or more other target nucleic acids in a manner which overcomes the problems noted above.

SUMMARY OF THE INVENTION

The problems noted above are overcome with methods which significantly enhance the performance of multiplex PCR reactions. The present invention provides methods and reagents for enhanced performance of multiplex PCR reactions. Such efficient conditions for multiplex PCR amplification involved the use of a hot-start DNA polymerase within the PCR reaction in combination with a volume excluding reagent. The positive effect on multiplex PCR is due on one hand to the use of a hot-start enzyme, which maximizes PCR efficiency by minimizing unwanted non-specific hybridisation and extension of primers or formation of primer-dimers. On the other hand, the presence of a volume excluding reagent enhances the hybridisation rate of all primers within the reaction. The presence of a volume excluding reagent in the reaction results in significantly increased product yield of targets that exhibit poor amplification under multiplex PCR conditions (limited primer concentrations) in the absence of the volume excluding reagent.

Surprisingly, it has been found that it is possible to perform multiplex PCR using even equimolar concentrations of all primers. According to the invention product yield from targets that exhibit poor amplification can be increased to acceptable levels by the use of a volume excluding reagent in combination with a hot-start DNA polymerase.

The described effect can only be achieved by the combination of both, the hot-start polymerase and the volume exclusion reagent.

The observed effect was surprising because the state of the art suggests that the positive effect of the use of volume excluding agents in co-amplification reactions is limited to certain hybridisation conditions, where strong differences in copy number between the target nucleic acids are observed (approx. 1000×difference as described in U.S. Pat. No. 5,705, 366). However, the PCR enhancing effect of the volume excluding reagent in combination with a hot-start DNA polymerase is surprisingly also observed when targets are present at comparable copy numbers ($\leq$10×difference).

DESCRIPTION OF THE DRAWINGS

The gel pictures both show in lane 1-8 data from duplicate reactions performed using a hot-start DNA polymerase (HotStarTaq, Qiagen) and in lanes 9-16 data of reactions performed using a standard thermostable DNA polymerase without hot-start (Taq DNA Polymerase, Qiagen).

In FIG. 1, reactions were carried out in the absence of Dextran with an average molecular weight of 35.000-45.000 dalton. (Lane 1+2 and lane 9+10, 0 wt-% Dextran) or in the presence of increasing concentrations of Dextran (Lane 3+4, 11+12: 1 wt-% Dextran, lane 5+6, 13+14: 3 wt-% Dextran, lane 7+8, 15+16: 6 wt-% Dextran).

In FIG. 2, reactions were carried out in the absence of PEG-8000 (Lane 1+2 and lane 9+10, 0 wt-% PEG-8000) or in the presence of increasing concentrations of PEG-8000 (Lane 3+4, 11+12: 1 wt-% PEG-8000, lane 5+6, 13+14: 3 wt-% PEG-8000, lane 7+8, 15+16: 6 wt-% PEG-8000).

Arrows on the left side of the picture identify the PCR products, that exhibit substantial increase in intensity when reactions were performed in the presence of the volume excluding reagent.

Data of densitometric analysis of the agarose gel pictures of example 1 are summarized for comparison in Table 2. Data from the agarose gel picture shown for example 2 are given in Table 3.

DESCRIPTION OF THE PREFERRED EMBODIMENTS OF THE INVENTION

The general principles and conditions for amplification and detection of nucleic acids using polymerase chain reaction are quite well known, the details of which are provided in numerous references including U.S. Pat. Nos. 4,683,195, 4,683,202 and 4,965,188 (noted above), all of which are incorporated herein by reference. Thus, in view of the teaching in the art and the specific teaching provided herein, a worker skilled in the art should have no difficulty in practicing the present invention by making the adjustments taught herein to co-amplify two or more nucleic acids, one of which is preferably a low copy target nucleic acid or is preferentially amplified.

To aid in understanding the invention, several terms are defined below.

The term "adjacent" as used herein refers to the positioning of the primer with respect to the probe on its complementary strand of the template nucleic acid. The primer and probe may be separated by 1 to about 20 nucleotides, more preferably, about 1 to 10 nucleotides, or may directly abut one another, as may be desirable for detection with a polymerization-independent process. Alternatively, for use in the polymerization-dependent process, as when the present method is used in the PCR amplification and detection methods as taught herein, the "adjacency" may be anywhere within the sequence to be amplified, anywhere downstream of a primer such that primer extension will position the polymerase so that cleavage of the probe occurs.

The term "hybridization" or "annealing", as used herein, refers to the formation of a duplex structure by two single stranded nucleic acids due to complementary base pairing. Hybridization can occur between complementary nucleic acid strands or between nucleic acid strands that contain minor regions of mismatch. Stability of a nucleic acid duplex is measured by the melting temperature, or "$T_m$." The $T_m$ is the temperature (under defined ionic strength and pH) at which 50% of the base pairs have dissociated. Those skilled in the art of nucleic acid technology can determine duplex stability empirically considering a number of variables including, for example, the length of the oligonucleotide, base composition and sequence of the oligonucleotide, ionic strength, and incidence of mismatched base pairs.

Conditions under which only fully complementary nucleic acid strands will hybridize are referred to as "stringent hybridization conditions" or "stringent annealing conditions". Stringent hybridization conditions are well known in the art (see, e.g., Sambrook et al., 1985, Molecular Cloning—A Laboratory Manual, Cold Spring Harbor Laboratory, Cold Spring Harbor, N.Y. Generally, stringent conditions are selected to be about 5° C. lower than the $T_m$ for the specific sequence at a defined ionic strength and pH. Typically, stringent conditions will be those in which the salt concentration is at least about 0.2 molar at pH 7 and the temperature is at least about 60° C. Relaxing the stringency of the hybridizing conditions will allow sequence mismatches to be tolerated; the degree of mismatch tolerated can be controlled by suitable adjustment of the hybridization conditions.

The term "label" as used herein refers to any atom or molecule which can be used to provide a detectable (preferably quantifiable) signal, and which can be attached to a nucleic acid or protein. Labels may provide signals detectable by fluorescence, radioactivity, colorimetry, gravimetry, X-ray diffraction or absorption, mass spectrometry, magnetism, enzymatic activity, and the like.

The term "melting temperature" as defined herein refers to the temperature at which one-half of a primer is denatured from a complementary strand (such as the template). The determination of the melting temperatures can be accomplished using several standard procedures, based on ultraviolet hypochromism, for example, by monitoring the spectrum at 260 nm as described in Biochemistry-The Molecular Basis of Cell Structure and Function, 2d Edition, Lehninger, Worth Publishers, Inc., 1970, pp. 876-7. The various methods of determining melting temperatures may produce slightly differing values for the same DNA molecule, but those values should not vary by more than about 2 or 3° C. Moreover, the difference between $T_mL$ and $T_mH$ should not vary within a given method for determining melting temperatures.

As defined herein, "5'->3' nuclease activity" or "5' to 3' nuclease activity" refers to that activity of a template-specific nucleic acid polymerase including either a 5'->3' exonuclease activity traditionally associated with some DNA polymerases whereby nucleotides are removed from the 5' end of an oligonucleotide in a sequential manner, (i.e., E. coli DNA polymerase I has this activity whereas the Klenow fragment does not), or a 5'->3' endonuclease activity wherein cleavage occurs more than one phosphodiester bond (nucleotide) from the 5' end, or both.

The terms "nucleic acid" and "oligonucleotide", as used herein, refer to primers, probes, and oligomer fragments to be detected, and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases. There is no intended distinction in length between the term "nucleic acid" and "oligonucleotide", and these terms will be used interchangeably. These terms refer only to the primary structure of the molecule. Thus, these terms include double- and single-stranded DNA, as well as double- and single-stranded RNA.

The term "sequence-specific probe" refer to probes that include fluorescer and quencher molecules attached to the oligonucleotide. As used herein, the terms "quenching" or "fluorescence energy transfer" refer to the process whereby when a fluorescer molecule and a quencher molecule are in close proximity, whenever the fluorescer molecule is excited, a substantial portion of the energy of the excited state nonradiatively transfers to the quencher where it either dissipates nonradiatively or is emitted at a different emission wavelength than that of the fluorescer. It is well known that the efficiency of quenching is a strong function of the proximity of the fluorescer and the quencher, i.e., as the two molecules get closer, the quenching efficiency increases. As quenching is strongly dependent on the physical proximity of the reporter molecule and quencher molecule, it has been assumed that the quencher and reporter molecules must be attached to the probe within a few nucleotides of one another, usually with a separation of about 6-16 nucleotides, e.g. Lee et al. Nucleic Acids Research, 21: 3761-3766 (1993); Mergny et al, Nucleic Acids Research, 22: 920-928 (1994); Cardullo et al, Proc. Natl. Acad. Sci., 85: 8790-8794 (1988); Clegg et al, Proc. Natl. Acad. Sci., 90: 2994-2998 (1993); Ozaki et al, Nucleic Acids Research, 20: 5205-5214 (1992); and the like. Typically, this separation is achieved by attaching one member of a reporter-quencher pair to the 5' end of the probe and the other member to a base 6-16 nucleotides away.

Because mononucleotides are reacted to make oligonucleotides in a manner such that the 5' phosphate of one mononucleotide pentose ring is attached to the 3' oxygen of its neighbour in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

The exact size of an oligonucleotide depends on many factors and the ultimate function or use of the oligonucleotide. Oligonucleotides can be prepared by any suitable method, including, for example, cloning and restriction of appropriate sequences and direct chemical synthesis by a method such as the phosphotriester method of Narang et al., 1979, Meth. Enzymol. 68:90-99; the phosphodiester method of Brown et al., 1979, Meth. Enzymol. 68:109-151; the diethylphosphoramidite method of Beaucage et al., 1981, Tetrahedron Lett. 22:1859-1862; and the solid support method of U.S. Pat. No. 4,458,066. A review of synthesis methods is provided in Goodchild, 1990, Bioconjugate Chemistry 1(3): 165-187.

Two single-stranded nucleic acids that are complementary except for minor regions of mismatch are referred to as "substantially complementary". Stable duplexes of substantially complementary sequences can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs.

The term "PCR reagent" refers to any of the reagents generally used in PCR, namely a set of primers for the opposing strands of each target nucleic acid, a DNA polymerase, a DNA polymerase cofactor, and two or more deoxyribonucleoside-5'-triphosphates (dNTP's).

The PCR reagents described herein are provided and used in PCR in suitable concentrations to provide amplification of the target nucleic acid. The minimal amount of DNA polymerase is generally at least about 1 unit/100 µl of solution, with from about 4 to about 25 units/100 µl being preferred. A "unit" is defined herein as the amount of enzyme activity required to incorporate 10 nmoles of total nucleotides (dNTP's) into an extending nucleic acid chain in 30 minutes at 74° C. The concentration of each primer is at least about 0.025 µmolar and less than about 1 µmolar with from about 0.05 to about 0.2 µmolar being preferred. All primers are present in about the same amount (within a variation of 10% of each). The cofactor is generally present in an amount of from about 1 to about 15 mmolar, and each dNTP is generally present at from about 0.15 to about 3.5 mmolar in the reaction mixture. The volume exclusion agent is present in an amount of at least about 1 weight percent, with amounts within the range of from about 1 to about 20 weight % being preferred. As used in defining the amounts of materials, the term "about" refers to a variation of +/−10% of the indicated amount.

The PCR reagents can be supplied individually, or in a buffered solution having a pH in the range of from about 7 to about 9 using any suitable buffer. Thus, a reaction mixture for PCR can contain a set of primers for each target nucleic acid such as low copy target nucleic acid, a set of primers for each high copy target nucleic acid, optional sequence-specific probes, suitable dNTP's, a thermostable DNA polymerase, a cofactor for the DNA polymerase, one or more volume exclusion agents, and any other addenda that one skilled in the art would consider useful in the amplification or eventual detection of the target nucleic acids.

The term "primer" refers to an oligonucleotide, whether natural or synthetic, capable of acting as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. Oligonucleotide analogues, such as "peptide nucleic acids", can act as primers and are encompassed within the meaning of the term "primer" as used herein. A primer is preferably a single-stranded oligodeoxyribonucleotide. The appropriate length of a primer depends on the intended use of the primer but typically ranges from 6 to 50 nucleotides. Short primer molecules generally require cooler temperatures to form sufficiently stable hybrid complexes with the template. A primer need not reflect the exact sequence of the template but must be sufficiently complementary to hybridize with a template. Primers can incorporate additional features which allow for the detection or immobilization of the primer but do not alter the basic property of the primer, that of acting as a point of initiation of DNA synthesis. For example, non-complementary sequences can be located at the ends of the primer to provide restriction enzyme cleavage sites useful in the cloning of an amplified sequence.

The term "reaction mixture" refers to a solution containing reagents necessary to carry out a given reaction. An "amplification reaction mixture", which refers to a solution containing reagents necessary to carry out an amplification reaction refers, as used herein, to an aqueous solution comprising the various amplification reagents used to amplify a target nucleic acid. The reagents include primers, enzymes, aqueous buffers, salts, target nucleic acid, and deoxynucleoside triphosphates (both conventional and unconventional). Depending on the context, the mixture can be either a complete or incomplete reaction mixture. A "PCR reaction mixture" typically contains oligonucleotide primers, a thermostable DNA polymerase, dNTP's, and a divalent metal cation in a suitable buffer.

A reaction mixture is referred to as complete if it contains all reagents necessary to enable the reaction, and incomplete if it contains only a subset of the necessary reagents. It will be understood by those of skilled in the art that reaction components are routinely stored as separate solutions, each containing a subset of the total components, for reasons of convenience, storage stability, and to allow for independent adjustment of the concentrations of the components depending on the application, and, furthermore, that reaction components are combined prior to the reaction to create a complete reaction mixture.

A typical PCR reaction mixture according to the invention minimally contains one or more sets of primers for the target nucleic acids, a thermostable DNA polymerase (as defined above), a plurality of dNTP's (such as the conventional four dNTP's) and one or more water-soluble or water-swellable, nonionic, polymeric volume exclusion agents. As used herein, the term "probe" refers to a labeled oligonucleotide which forms a duplex structure with a sequence in the target nucleic acid, due to complementarity of at least one sequence in the probe with a sequence in the target region. The probe, preferably, does not contain a sequence complementary to sequence(s) used to prime the polymerase chain reaction. Generally the 3' terminus of the probe will be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as a dideoxynucleotide.

The terms "target sequence" and "target nucleic acid sequence", as used herein, refer to a region of the oligonucleotide which is to be amplified, detected, or both. The target sequence resides between the two primer sequences used for amplification.

The term "target nucleic acid" refers to nucleic acid that can be obtained from various sources including plasmids, and naturally occurring DNA or RNA from any source (such as bacteria, yeast, viruses, plants, higher animals or humans). It may be extracted from various tissues including blood, peripheral blood mononuclear cells (PBMC), other tissue materials or other sources known in the art using known procedures. The present invention is particularly useful for the co-amplification and detection of nucleic acid sequences found in genomic DNA, bacterial DNA, proviral DNA, fungal DNA, viral RNA, or DNA or RNA found in bacterial or viral infected cells, animal cells, plant cells or human cells.

Various procedures are known in the art, including those described by Laure et al. in The Lancet, pp. 538-540 (Sep. 3, 1988), Maniatis et al., Molecular Cloning: A Laboratory Manual, pp. 280-281 (1982), Gross-Belland et al in Eur. J. Biochem., 36, 32 (1973) and U.S. Pat. No. 4,965,188 (noted above). Extraction of DNA from whole blood or components thereof are described, for example, in EP-A-0 393 744, Bell et al, Proc. Natl. Acad. Sci. USA, 78(9), pp. 5759-5763 (1981), Saiki et al, Bio/Technology, 3, pp.1008-1012 (1985) and U.S.

Pat. No. 5,231,015 (Cummins et al.). The particular extraction procedure is not essential to the practice of the present invention.

Since the target nucleic acid to be amplified and detected is usually in double strand form, the two strands must be separated (that is, denatured) before priming can take place. This can occur during the extraction process, but preferably, it occurs in a separate step afterwards. Heating to a suitable temperature (identified as "first temperature") is a preferred means for denaturation. Generally, this first temperature is in the range of from about 85 to about 100° C. for a suitable time, for example from 1 to about 240 seconds (preferably 1 to about 40 seconds). This initial denaturation step can also be included in the first amplification cycle. In such instances, denaturation may be longer in the first cycle (for example, up to 240 seconds) whereas later cycles can have much shorter denaturation steps (for example, up to 30 seconds).

The term "thermostable DNA polymerase" refers to an enzyme that is relatively stable to heat and catalyzes the polymerization of nucleoside triphosphates to form primer extension products that are complementary to one of the nucleic acid strands of the target sequence. The enzyme initiates synthesis at the 3' end of the primer and proceeds in the direction toward the 5' end of the template until synthesis terminates. Purified thermostable DNA polymerases can be selected from the genera *Thermus, Pyrococcus Thermococcus* and *Thermotoga*, preferably *Thermus aquaticus, Pyrococcus furiosus, Pyrococcus woesei, Pyrococcus* spec. (strain KOD1), *Pyrococcus* spec. GB-D, *Thermococcus Litoralis Thermococcus* sp. 9. degree. N-7, *Thermotoga maritima, Pyrococcus* spec. ES4 (endeavori), *Pyrococcus* spec. OT3 (horikoshii), *Pyrococcus profundus, Thermococcus stetteri, Thermococcus* spec. AN1 (zilligii), *Thermococcus peptonophilus, Thermococus celer* and *Thermococcus fumicolans*. The term "thermostable enzyme" refers to an enzyme that is relatively stable to heat. The thermostable enzymes can withstand the high temperature incubation used to remove the modifier groups, typically greater than 50° C., without suffering an irreversible loss of activity. Modified thermostable enzymes usable in the methods of the present invention include thermostable DNA polymerases and thermostable ligases.

The term "test specimen" refers to cellular or viral material, hair, body fluids or other materials containing genomic DNA or RNA which can be detected.

The terms "upstream" and "downstream", as used herein, refer to the location of the primer binding sites along the target sequence. The upstream primer hybridizes to the non-coding strand of the target sequence, and therefore forms the 5' end of the amplified sequence which is a subsequence of the coding strand of the target sequence. Similarly, the downstream primer hybridizes to the coding strand of the target sequence, and therefore forms the 3' end of the amplified sequence which is a subsequence of the non-coding strand of the target sequence.

The term "volume exclusion agent", as defined herein, refers to one or more water-soluble or water-swellable, non-ionic, polymeric volume exclusion agents.

The volume exclusion agents are polymeric, meaning that they typically comprise a plurality of repeating units, and generally have an average molecular weight of from about 1000 to about 2,000,000 daltons, with a molecular weight in the range of from about 3000 to about 500,000 daltons being preferred.

Useful classes of materials which can be used as volume exclusion agents in the practice of this invention include, but are not limited to, polyethers, reaction products of a simple sugar (such as dextrose or glucose) with epichlorohydrin, polysaccharides, polyacrylates and similar materials readily apparent to one skilled in the art.

According to the invention polyethers are preferred. They can be generally represented by the formula:

wherein R is divalent alkylene bridge of 1 to 6 carbon atoms—branched or unbranched—and n is an integer of 15 to 1000 (weight average basis). For example, R can be 1,2-ethylene, 1,3-propylene, 1,2-propylene, 2-hydroxy-1,3-propylene, 3-hydroxy-1,2-propylene, 1,4-butylene, 1,3-butylene, 1,2-hexylene and other divalent alkylene groups which would be readily apparent to one skilled in the art. Preferably, R is 1,2-ethylene or 1,2-propylene as in poly(ethylene oxide) or poly(propylene oxide), which are commonly known as poly(ethylene glycol) and poly(propylene glycol), respectively.

In the noted formula, the integer "n" represents the weight average molecular weight of the compound divided by the monomeric unit molecular weight. For the preferred compounds noted in the preceding paragraph, the average molecular weights are at least about 1000, preferably at least about 3000, and generally up to about 20,000. One skilled in the art can readily determine the appropriate "n" number of units for a given compound and compound weight. Generally, n is an integer of from 15 to 1000. As used in defining the molecular weights, the term "about" refers to a variance of +/−10%.

The volume exclusion agent is used in an amount of 1%-20%, preferably 1-15%, most preferably 1-8% by weight.

Most preferred is a poly(ethylene glycol) having an average molecular weight about 8000 (PEG 8000) is used in an amount of 1%-20%, preferably 1-15%, most preferably 1-8% by weight.

Also included within the definition of polyethers are condensation products of ethylene oxide, propylene oxide or other alkylene oxides or various moieties such as diols, triols, sugars or acids, including polyglycidols. Such materials are well known in the art as nonionic surfactants or detergents and may be useful in the present invention provided the requisite water solubility or water swellability parameters are met.

Another preferred volume exclusion reagent according to the invention is dextran. Dextran is a bacterial byproduct; the dextran macromolecule consists of end-to-end linked glucan groups. Biosynthesis of dextran has been demonstrated in numerous bacteria, especially in *Streptococcus mutans, Leuconostoc mesenteroides* ssp. *mesenteroides* and *Leuconostoc mesenteroides* ssp. *dextranicum*. Different molecular weights can be generated by limited hydrolysis and fractionation of the molecule. For example the native, high molecular dextran ($M_r$ $1.5 \times 10^4$–$5 \times 10^7$, which is built up from α-D-glucose can be hydrolysed—after a purification by precipitation with methanol or acetone—under acid conditions at temperatures in range of 100° C. to molecular weight fractions in the range of 40.000 to 60.000 [Römpp, Lexikon der Biochemie und Molekularbiologie, Georg Thieme Verlag, Stuttgart, 2000, and literature cited therein]).

Nonionic polysaccharides useful in the practice of this invention include glycogen and others readily apparent to one skilled in the art.

Examples of useful polyacrylates include, but are not limited to, poly(hydroxyethyl acrylate), poly(2,3-dihydroxypropyl acrylate) and others readily apparent to one skilled in the art.

The amplification method of this invention is preferably conducted in a continuous, automated manner so that the reaction mixture is temperature cycled in a controlled manner for a desired number of times. A number of instruments have been developed for this purpose, as one of ordinary skill in the art would know. Preferably, the instrument used will also be programmable for both primary and secondary amplification cycles.

One such instrument for this purpose is described in some detail in U.S. Pat. No. 4,965,188 and EP-A-0 236,069. Generally, this instrument includes a heat conducting container for holding a number of reaction tubes containing reaction mixture, a means for heating, cooling and temperature maintenance, and a computing means to generate signals to control the amplification sequence, changes in temperature and timing.

EP-A-0 402 994 provides details of useful chemical test packs which can be processed using the instrument described in U.S. Pat. No. 5,089,233 (Devaney, Jr. et al.), incorporated herein by reference. Also described therein are means for heating and cooling the test pack at repeated intervals (that is, through cycles) appropriate for the method of the present invention. Further details regarding useful PCR processing equipment can be obtained from the considerable literature in the field, and would be readily known by one skilled in the art.

Besides chemical test packs described above, the method can be carried out in other containers such as those described in more detail in U.S. Pat. No. 4,902,624 (Columbus et al), U.S. Pat. No. 5,173,260 (Zander et al) and U.S. Pat. No. 5,229,297 (Schnipelsky et al), all incorporated herein by reference, and any other suitable container which is readily apparent to one skilled in the art. Such test packs are also known as self-contained test devices which have separate compartments for various reagents used in the method of this invention. The compartments are appropriately connected so reagents and assay solutions can be brought into contact with the capture reagent at appropriate times without opening the device.

Detection of amplified products can be accomplished using any known procedure, including Southern blotting techniques, as described in U.S. Pat. No. 4,965,188 (noted above), or by use of labeled probes or primers, as is known in the art.

Alternatively to the embodiments described above, the amplified products can be detected using a labeled oligonucleotide which is complementary to one of the primer extension products. Procedures for attaching labels to oligonucleotides are well known. Useful labels include enzymes, ferritin and other magnetic particles, cleavable masstags, radioisotopes, chemiluminescent reagents (for example, luminol), biotin and various fluorogens and chromogens. Useful enzyme labels include glucose oxidase, peroxidase and alkaline phosphatase. Substrates and dye providing reagents for various labels, such as enzymes, are also known.

Preferred is the detection of PCR products by fluorescense using intercalating fluorescent dyes such as ethidium bromide or SYBR Green® and employing fluorescent labelled sequence-specific probes or fluorescent labelled primers.

It is also possible that one of the primers of each primer set used in the method is labeled with a specific binding moiety. This moiety can be the same or different for various primers, and include any molecule for which there is a specific binding receptor which reacts specifically with that moiety. Examples of specific binding pairs (one of which can be the label) include, but are not limited to, streptavidin/biotin, sugar/lectin, antibody/hapten, antibody/antigen and others readily apparent to one skilled in the art. The receptor molecule is then conjugated with a suitable detectable label moiety such as an enzyme, radioisotope or others described above for oligonucleotides.

More preferably, one or both primers of each primer set are labeled with biotin (or an equivalent derivative thereof), and the amplified product is detected using a conjugate of streptavidin and an enzyme, such as horseradish peroxidase.

Most preferred, however, are primers carrying a fluorescent dye.

In heterogeneous detection systems of this invention, the amplified products are captured on a water-insoluble substrate of some kind, and the other materials in the reaction mixture are removed in a suitable manner, such as by filtration, centrifugation, washing or another separation technique.

Capture probes can be attached to water-insoluble supports using known attachment techniques (including absorption and covalent reactions). One such technique is described in EP-A-0 439 222 (published Sep. 18, 1991) Other techniques are described, for example, in U.S. Pat. No. 4,713,326 (Dattagupta et al), U.S. Pat. No. 4,914,210 (Levenson et al) and EP-B-0 070 687 (published Jan. 26, 1983). Useful separation means include filtration through membranes such as polyamide microporous membranes commercially available from Pall Corporation.

However, any useful solid support can be used to anchor the capture probe and eventual hybridization product, including microtiter plates, test tubes, beakers, magnetic or polymeric particles, metals, ceramics, and glass wool to name a few. Particularly useful materials are magnetic or polymeric particles having reactive groups useful for covalently attaching the capture probe. Such particles are generally from about 0.001 to about 10 µm meters. Further details about examples of such materials are provided in U.S. Pat. No. 4,997,772 (Sutton et al), U.S. Pat. No. 5,147,777 (Sutton et al), U.S. Pat. No. 5,155,166 (Danielson et al) and U.S. Pat. No. 4,795,698 (Owen et al), all incorporated herein by reference.

The capture probe can be affixed to a flat support such as a polymeric film, membranes, filter papers, or resin-coated or uncoated paper. Capture probe affixed to polymeric particles can also be immobilized on such flat supports in a suitable manner, for example, as dried deposits, or adhered by heat fusion or with adhesives. The capture probe can be affixed, for example, to a flat support in the self-contained test device of this invention. Other details of such materials are provided in EP-A-0 408 738 (published Jan. 23, 1991), WO 92/16659 (published Oct. 1, 1992) and U.S. Pat. No. 5,173,260 (Sutton et al).

The capture probes can be arranged on a suitable support in any configuration, for example rows of round deposits or stripes.

The present invention can also be used in what are known as "homogeneous" amplification procedures in which multiple target nucleic acids are simultaneously detected without the need for capture reagents. The details of such assays are known in the art, such as EP-A-0 487 218 (published May 27, 1992) and EP-A-0 512 334 (published Nov. 11, 1992).

The amplification reaction composition of this invention can be included as one individually packaged component of a kit useful for various amplification assays. The kit can include other reagents, solutions, equipment and instructions useful in the method of this invention, including capture reagents immobilized on a water-insoluble substrate, wash solutions, extraction solutions, detection reagents and other materials readily apparent to one skilled in the art.

The problems noted above are overcome with a method for the coamplification of two or more target nucleic acids, the method comprising at least 15 primary amplification cycles, each primary amplification cycle—as it is described by U.S. Pat. No. 5,705, 366 which is incorporated by reference—comprising the sequential steps of:
A) heating a reaction mixture of two or more target nucleic acids, or their primer extension products, at a first temperature, $T_1$, for denaturation of the strands of the target nucleic acids or their primer extension products,
B) priming the denatured strands with a set of unmodified or modified (e.g. carrying a fluorophore moiety) primers specific to and hybridizable with opposing strands of each target nucleic acid to be amplified, by cooling to a second temperature, $T_2$, and
C) either as a continuation of step B) or in a separate step, forming primer extension products in a reaction mixture of PCR reagents, by incubation at a third temperature, $T_3$, provided that when priming and primer extension product formation are carried out in the same step, $T_2$ and $T_3$ are the same,
wherein the reaction mixture in at least one of the primary amplification cycles comprises from 1 to 20 weight %, preferably 1 to 15 weight %, most preferably 1 to 8 weight %, of a nonionic, polymeric volume exclusion agent and a DNA polymerase.

This invention also provides a method for the coamplification of two or more target nucleic acids and detection of one of more of the target nucleic acids, the method comprising at least 15 primary amplification cycles, each primary amplification cycle comprising the sequential steps of:
(A) heating a reaction mixture of two or more target nucleic acids, or their primer extension products, at a first temperature, $T_1$, for denaturation of the strands of the target nucleic acids or their primer extension products,
(B) priming the denatured strands with a set of primers specific to and hybridizable with opposing strands of each target nucleic acid to be amplified, by cooling to a second temperature, $T_2$,
(C) either as a continuation of step (B) or in a separate step, forming primer extension products in a reaction mixture of PCR reagents, by incubation at a third temperature, $T_3$, provided that when priming and primer extension product formation are carried out in the same step, $T_2$ and $T_3$ are the same,
wherein the reaction mixture in at least one of the primary amplification cycles comprises from 1 to 20 weight %, preferably 1 to 15 weight %, most preferably 1 to 8 weight %, of a nonionic, polymeric volume exclusion agent, a DNA Polymerase and,
(D) after the last primary amplification cycle, detecting one or more of the primer extension products as an indication of one or more of the target nucleic acids.

Moreover, an amplification reaction composition which is buffered to a pH of from about 7.5 to about 9, comprises:
one or more sets of primers,
a thermostable DNA polymerase,
a plurality of dNTP's, and
1 to 20 weight %, preferably 1 to 15 weight %, most preferably 1 to 8 weight %, of a nonionic, polymeric volume exclusion agent.

Additionally, this invention provides a process comprising the sequential steps of:
(A) heating a reaction mixture of two or more target nucleic acids, or their primer extension products, at a first temperature, $T_1$, for denaturation of the strands of the target nucleic acids or their primer extension products,
(B) priming the denatured strands with a set of unmodified or modified (e.g. carrying a fluorophore moiety) primers specific to and hybridizable with opposing strands of each target nucleic acid to be amplified, by cooling to a second temperature, $T_2$, and
(C) either as a continuation of step (B) or in a separate step, forming primer extension products in a reaction mixture of PCR reagents, by incubation at a third temperature, $T_3$, provided that when priming and primer extension product formation are carried out in the same step, $T_2$ and $T_3$ are the same,
wherein the reaction mixture in at least one of the primary amplification cycles comprises from 1 to 20 weight %, preferably 1 to 15 weight %, most preferably 1 to 8 weight %, of a nonionic, polymeric volume exclusion agent, a hot start DNA Polymerase and a sequence specific probe which binds within the primer binding regions and which generates a fluorescent signal after hybridisation.

This invention also provides a method for the coamplification of two or more target nucleic acids and detection of one of more of the target nucleic acids, the method comprising at least 15 primary amplification cycles, each primary amplification cycle comprising the sequential steps of:
(A) heating a reaction mixture of two or more target nucleic acids, or their primer extension products, at a first temperature, $T_1$, for denaturation of the strands of the target nucleic acids or their primer extension products,
(B) priming the denatured strands with a set of primers specific to and hybridizable with opposing strands of each target nucleic acid to be amplified, by cooling to a second temperature, $T_2$,
(C) either as a continuation of step (B) or in a separate step, forming primer extension products in a reaction mixture of PCR reagents, by incubation at a third temperature, $T_3$, provided that when priming and primer extension product formation are carried out in the same step, $T_2$ and $T_3$ are the same,
wherein the reaction mixture in at least one of the primary amplification cycles comprises from 1 to 20 weight %, preferably 1 to 15 weight %, most preferably 1 to 8 weight %, of a nonionic, polymeric volume exclusion agent, a hot start DNA Polymerase and a sequence specific probe which binds within the primer binding regions and which generates a fluorescent signal after hybridisation, and,
(D) in the course of the reaction in each amplification cycle or in an amplification cycle after the last primary amplification cycle, detecting one or more of the primer extension products as an indication of one or more of the target nucleic acids.

Moreover, an amplification reaction composition which is buffered to a pH of from about 7.5 to about 9, comprises:
one or more sets of primers,
a thermostable hot-start DNA polymerase,
a plurality of dNTP's, and
1 to 20 weight %, preferably 1 to 15 weight %, most preferably 1 to 8 weight %, of a nonionic, polymeric volume exclusion agent and a sequence specific probe, which binds within the primer binding regions and which generates a fluorescent signal after hybridisation.

A kit of this invention comprises, individually packaged or as a mixture having all or a part of the components:
(a) an amplification reaction composition buffered to a pH of from about 7.5 to about 9 and comprising:
optionally one or more sets of primers,
a thermostable hot-start DNA polymerase,
a plurality of dNTP's, and
1 to 20 weight %, preferably 1 to 15 weight %, most preferably 1 to 8 weight %, of a nonionic, polymeric volume exclusion agent,
(b) a capture reagent comprising an oligonucleotide immobilized on a water-insoluble substrate.

Still further, a self-contained test device comprises, in separate compartments:
(a) an amplification reaction composition buffered to a pH of from about 7.5 to about 9 and comprising:
one or more sets of primers,
a thermostable hot-start DNA polymerase,
a plurality of dNTP's, and
1 to 20 weight %, preferably 1 to 15 weight %, most preferably 1 to 8 weight %, of a nonionic, polymeric volume exclusion agent, and,
(b) a capture reagent comprising an oligonucleotide immobilized on a water-insoluble substrate, the compartments being connected in the test device so that the amplification reaction composition can be brought into contact with the capture reagent after amplification without opening the test device.

The present invention provides a very rapid and efficient method for preferentially amplifying a nucleic acid in a mixture of one or more other nucleic acids which are being coamplified. For example, the invention can be used to preferentially amplify and detect a low copy target nucleic acid over amplified high copy target nucleic acids. In such instances, the inhibition of low copy target nucleic acid amplification by the high copy target nucleic acid, is reduced. In other instances, the invention can be used to manipulate the amplification of one target nucleic acid over the others for various reasons. In yet another example, co-amplification of target nucleic acids can be efficiently achieved even when the amplification of one or more target nucleic acids is preferred for reasons such as PCR product size and differences in efficiency of primer binding and extension.

The advantages of this invention are achieved by including a water-soluble or water-swellable, nonionic, polymeric volume exclusion agent within the amplification reaction mixture in at least one amplification cycle. The presence of this agent effectively allows the user to reduce the amount of primer needed for efficient amplification of the nucleic acids, allowing efficient coamplification in the presence of primer concentrations which can be as a rate limiting reactant or even in the presence of equimolar primer concentrations.

In addition, the volume exclusion agent also increases the rate of renaturation of the amplification reaction products which further reduces amplification efficiency for high copy target nucleic acids compared to the low copy target nucleic acids.

MATERIALS AND METHODS

Examples 1 and 2

The primers used in the examples 1 and 2 are specific for the murine genomic loci of PKC, SLP-65, ILGFMAR, c-fos, N-ras, fas, CD19 and CD5 und have the sequences given in table 1:

TABLE 1

Primer sequences and PCR product size of examples 1 and 2

| Primer sequence | SEQ ID NO: | Primer name | Product size [bp] | GC-content PCR product [%] |
| --- | --- | --- | --- | --- |
| GCTGCTTGAAGAAACGAGCGGTG | 1 | MPKC-3' | 1953 | 55.6 |
| CTGCACCTTCTGGAATTCCGACTC | 2 | MPKC-5' | | |
| ATGTGGTCCCTGTGGAAGATAACGA | 3 | Mslp65-5' | 1350 | 45 |
| GCGACATGTGCTTTGAGGAACTGTT | 4 | Mslp-65-3' | | |
| ATCCTCCTTCTATAGTCTGTCCAAGAGTAG | 5 | MILGFMAR2-5' | 332 | 18.7 |
| CCTCCAGAAAAAGCTAGATACTAACCTT | 6 | MILGFMAR2-3' | | |
| ATCAGGTGCGAATGTTCGCTCG | 7 | Mc-fos-5' | 477 | 61.4 |
| CTCGCTGCAGTCGCGGTTGGAG | 8 | Mc-fos-3' | | |
| TTGGGTTTGCAGGAATTGGAA | 9 | MN-RAS-5' | 192 | 46.4 |
| GTTTCTAAGGCACCCATTCGATACAC | 10 | MN-RAS-3' | | |
| CGCCTGTGCAGTGGTGAGTCAGTG | 11 | Mfas-5' | 1077 | 52.4 |
| ACTGGATTGAACCTCGGAGGGTCG | 12 | Mfas-3' | | |
| ACAGTGAACGTGGAGGATAGTGGTG | 13 | MCD19-5' | 750 | 54.5 |
| CCCAAGGCTTAGGCTCAGTAGTGA | 14 | MCD19-3' | | |
| AGATTATGGACTTCCAGCCCGTACAC | 15 | MCD5-5' | 623 | 57.1 |
| GTACCCAGTACCGGCAGAGACTCAC | 16 | MCD5-3' | | |

PCR was carried out using an automated MJ Research PTC-200 Thermocycler.

Hot startaq® (commercially available from QIAGEN GmbH, Hilden, Germany) was used as a hot-start DNA polymerase. This polymerase can be obtained according to U.S. Pat. No. 6,183,998, incorporated herein by reference, which discloses, in particular, that thermostable enzymes are reversibly modified in the presence of an aldehyde. The modified thermostable enzymes of that disclosure do not show significant increase in enzyme activity at 37° C., even when incubated for periods of an hour or more. On the other hand, enzymatic activity of the chemically modified enzymes is increased at least two-fold within thirty minutes when incubated at a more elevated temperature, i.e., above 50° C., preferably at a temperature of 75° C. to 100° C., and most preferably at 95° C. Such chemically modified enzymes may be employed in all applications involving manipulation of nucleic acids, such as amplification, ligation, exonucleolytic or endonucleolytic reactions, or nucleic acid topology changing enzymatic reactions, wherein the inactivated enzyme becomes reactivated by incubating the reaction mixture prior or as part of the intended enzymatic reaction at an elevated temperature. The preferred method of modification consists in crosslinking molecules of thermostable enzyme, e.g., Taq DNA polymerase, by reaction with formaldehyde. The formaldehyde-modified Taq DNA polymerase is useful for a hot-start PCR. Mouse genomic DNA from NIH 3T3 cells was used as a template.

The reactions were carried out in a reaction buffer containing Tris-HCl, pH 8.7, potassium chloride, ammonium sulphate, magnesium chloride, each dNTP, 2.5 U of the indicated heat-stable DNA polymerase and 0.2 µM of each of the forward and reverse primers given in Table 1.

Commercially available PEG-8000, a poly(ethylene glycol) having a molecular weight of about 8000 Dalton was used as volume excluding agent.

Also a commercially available Dextran (from *Leuconostoc mesenteroides*, obtained from Sigma) having an average molecular weight of 35.000-45.000 Dalton was used.

Table 2 shows in the upper panels a comparison of PCR product yield of reactions containing a hot-start polymerase and Dextran. Additionally, the increase (ratio of signals from samples with volume excluder divided by signal obtained without volume excluder) in signal intensity for the different conditions is shown. In the lower panels of Table 2 data for a non hot-start method are shown.

Figure 1:
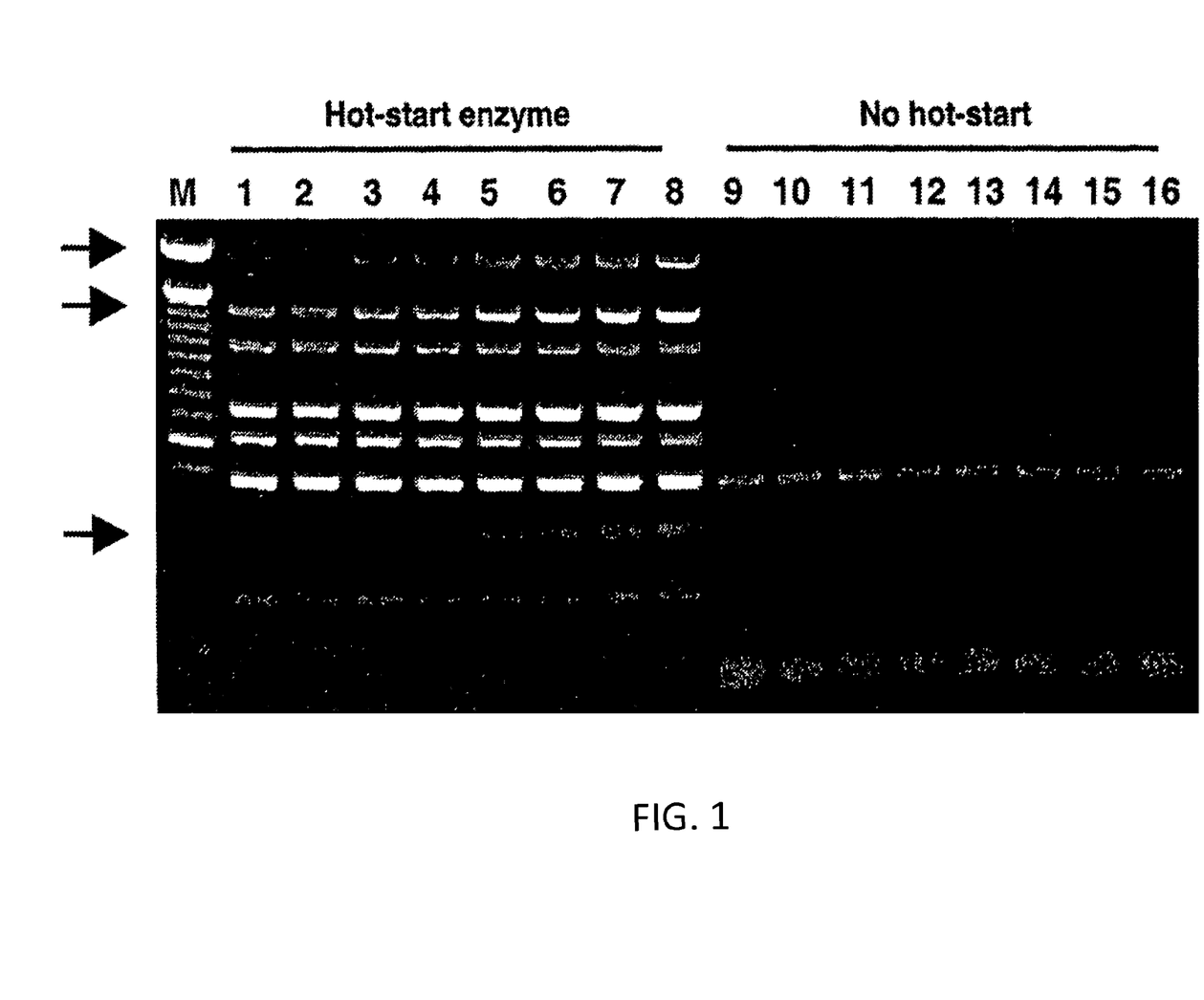
FIGS. 1 and 2 show data from agarose gel analysis of the 8-plex PCR products. Lanes are numbered from left to right. A size standard (100 bp ladder, Invitrogen) was loaded in the lane labelled with M.
Figure 2:
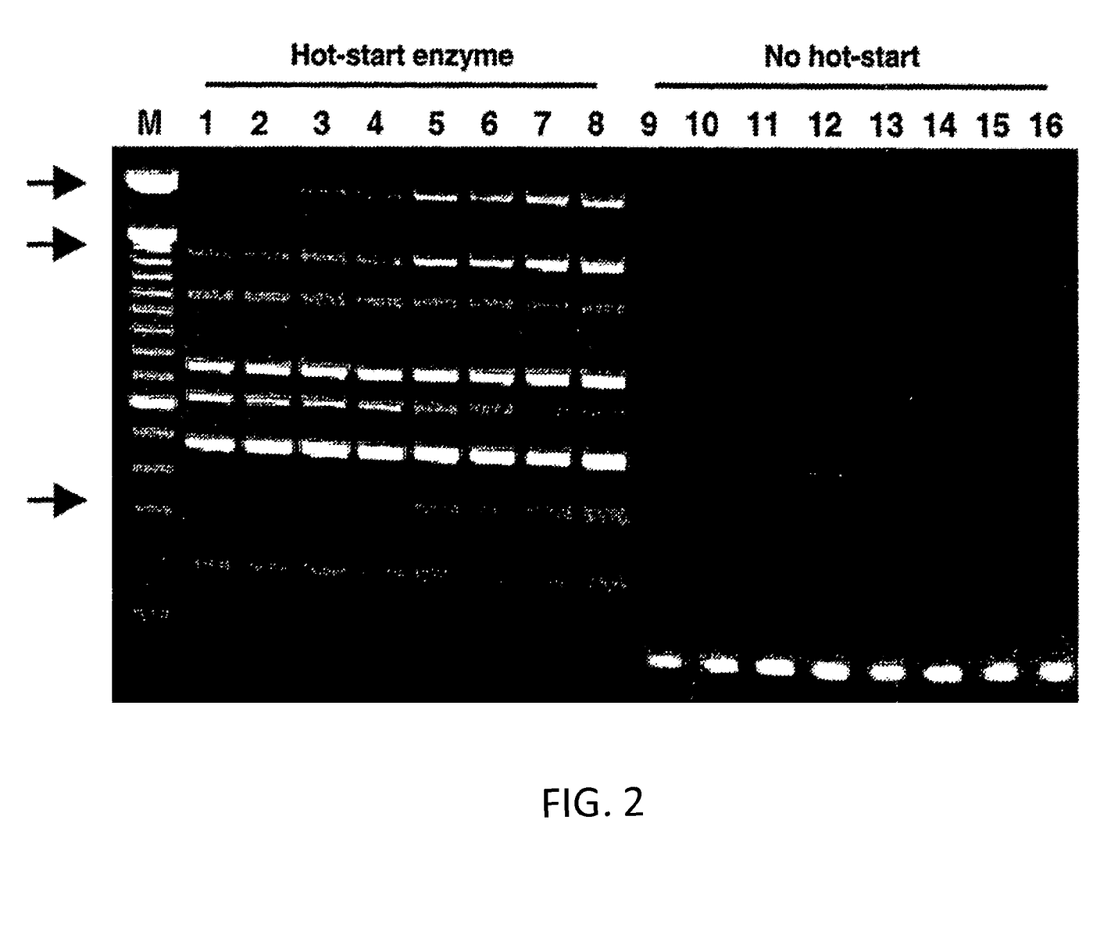

The upper panels of Table 3 show a comparison of PCR product yield of reactions containing a hot-start polymerase and PEG-8000. Ratio of signals from samples with volume excluder divided by signal obtained without volume excluder in signal intensity for the different conditions is shown. The designator "N.D." in Table 2 and Table 3 stands for "not determinable" because, as noticeable in FIG. 1, no or not sufficient product was generated for an analysis.

TABLE 2

| | Dextran [wt-%] | | | | | | |
|---|---|---|---|---|---|---|---|
| | 0% | 1% | | 3% | | 6% | |
| Product size | signal | signal | fold increase* | signal | fold increase* | signal | fold increase* |
| HotStarTaq | | | | | | | |
| 1953 | 9 | 19 | 2.11 | 42 | 4.61 | 55 | 6.06 |
| 1350 | 35 | 48 | 1.37 | 68 | 1.93 | 78 | 2.21 |
| 1077 | 42 | 49 | 1.17 | 50 | 1.18 | 46 | 1.10 |
| 750 | 84 | 86 | 1.03 | 89 | 1.06 | 94 | 1.13 |
| 623 | 59 | 65 | 1.11 | 57 | 0.97 | 54 | 0.91 |
| 477 | 93 | 92 | 0.98 | 97 | 1.04 | 97 | 1.04 |
| 332 | 10 | 14 | 1.47 | 27 | 2.84 | 43 | 4.53 |
| 192 | 28 | 32 | 1.13 | 36 | 1.27 | 40 | 1.43 |
| Taq | | | | | | | |
| 1953 | N.D. | N.D. | N.D. | N.D. | N.D. | N.D. | N.D. |
| 1350 | N.D. | N.D. | N.D. | N.D. | N.D. | N.D. | N.D. |
| 1077 | N.D. | N.D. | N.D. | N.D. | N.D. | N.D. | N.D. |
| 750 | 28 | 9 | 0.32 | 10 | 0.36 | 12 | 0.43 |
| 623 | N.D. | N.D. | N.D. | N.D. | N.D. | N.D. | N.D. |
| 477 | 28 | 48 | 1.70 | 48 | 1.70 | 42 | 1.48 |
| 332 | N.D. | N.D. | N.D. | N.D. | N.D. | N.D. | N.D. |
| 192 | N.D. | N.D. | N.D. | N.D. | N.D. | N.D. | N.D. |

*fold increase compared to samples with 0% Dextran

TABLE 3

| | PEG-8000 [wt-%] | | | | | | |
|---|---|---|---|---|---|---|---|
| | 0% | 1% | | 3% | | 6% | |
| Product size | signal | signal | fold increase* | signal | fold increase* | signal | fold increase* |
| HotStarTaq | | | | | | | |
| 1953 | 4 | 17 | 4.08 | 38 | 9.11 | 50 | 12.08 |
| 1350 | 13 | 29 | 2.19 | 46 | 3.46 | 64 | 4.87 |
| 1077 | 24 | 27 | 1.10 | 25 | 1.04 | 19 | 0.78 |
| 750 | 62 | 71 | 1.16 | 78 | 1.26 | 86 | 1.40 |
| 623 | 41 | 38 | 0.93 | 30 | 0.74 | 20 | 0.48 |
| 477 | 89 | 92 | 1.04 | 92 | 1.04 | 46 | 0.52 |
| 332 | 3 | 7 | 2.38 | 19 | 6.21 | 35 | 11.15 |
| 192 | 20 | 23 | 1.17 | 30 | 1.51 | 31 | 1.58 |
| Taq | | | | | | | |
| 1953 | N.D. | N.D. | N.D. | N.D. | N.D. | N.D. | N.D. |
| 1350 | N.D. | N.D. | N.D. | N.D. | N.D. | N.D. | N.D. |
| 1077 | N.D. | N.D. | N.D. | N.D. | N.D. | N.D. | N.D. |
| 750 | N.D. | N.D. | N.D. | N.D. | N.D. | N.D. | N.D. |
| 623 | N.D. | N.D. | N.D. | N.D. | N.D. | N.D. | N.D. |
| 477 | 5 | 14 | 2.55 | 9 | 1.65 | 6 | 1.13 |
| 332 | N.D. | N.D. | N.D. | N.D. | N.D. | N.D. | N.D. |
| 192 | N.D. | N.D. | N.D. | N.D. | N.D. | N.D. | N.D. |

*fold increase compared to samples with 0% PEG-8000

Example 3

Primers and sequence specific probes for the 5'-3' nuclease assay used in example 3 were specific for the human genomic loci CSBG and c-myc. Sequences are given in Table 4. Probes were modified at the 5' end with a fluorescent dye and at the 3' end with a Black Hole Quencher™, a non-fluorescent molecule that strongly quenches the fluorescence of the dye attached at the 5' end. Additionally, they contained at the 3'-end a phosphate group instead of the 3'-OH group to prevent extension by the DNA Polymerase. The probe for CSBG contained at the 5' end the fluorescent dye 6-FAM and a Black Hole Quencher 1™ attached to the 3' end. The probe for c-myc contained the dye HEX coupled the 5' and a Black Hole Quencher™ 1 at the 3' end.

TABLE 4

Sequences of primers and sequence specific probes and PCR product size of Example 3

| Primer sequence | SEQ ID NO: | Primer name | Product size [bp] |
|---|---|---|---|
| TTCTGTTTATATCTTTATTTTTAATCACCCC | 17 | CSBG-for | 100 |
| AGAAAGCTAAGCATTTATCTCAAGAAAATAG | 18 | CSBG-rev | |
| AAATTCTCTGGGTTTTGGTCTGTTGTGCTTTT | 19 | CSBG-TM | |
| CCCTATTCGCTCCGGATCTC | 20 | cmyc2 | 78 |
| GCCGGCTAGGGTGGAAGA | 21 | cmyc2 | |
| ACGCCCGCAGCGCAGCTC | 22 | c-myc2-TM | |

The reaction in example 3 were done using the QuantiTect Probe PCR Kit (QIAGEN) as reaction chemistry. A primer concentration of 0.2 µM of each of the forward and reverse primers and 0.2 µM of the sequence specific probes given in Table 4 were used.

Commercially available PEG-8000, a poly(ethylene glycol) having a molecular weight of about 8000 Dalton was used as volume excluding agent.

These results clearly demonstrate that the combined use of a volume excluding reagent and a hot-start polymerase in co-amplification reactions results in dramatically increased product yield of PCR products or increased PCR efficiency resulting in lower Ct values, that show poor amplification in the absence of the volume excluding reagent. The same effect was also observed with hot start enzymes which are either temporarily chemically activated such as HotStarTaq (Qiagen GmbH) as well as with antibody-blocked enzymes (data not shown). Negative effect of the volume excluding reagent on PCR products, that are already generated at sufficient yield in absence of the volume excluding reagent were not detectable (Table 2 and Table 3). In contrast, PCR efficiency of samples containing a standard Taq polymerase (Qiagen GmbH) without hot-start showed poor amplification efficiency, independent if the volume excluder was present or not. In example 1 and example 2, only one of the 8 PCR products was detectable at all.

Examples and reaction conditions are described below to demonstrate the course of the invention in practical use. These examples demonstrate the Multiplex PCR enhancing effect of volume excluding reagents which specifically improves PCR in combination with a hot-start DNA polymerase. However, the examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples. All percentages are by weight unless otherwise noted.

EXAMPLES

Examples 1 and 2

The effect of the combination of a hot-start DNA polymerase and a volume excluding reagent on multiplex PCR was studied in a reaction containing 8 different primer pairs specific for the murine genomic loci of PKC, SLP-65, ILG-FMAR, c-fos, N-ras, fas, CD19 and CD5 (see Table 3, referred to as 8-plex PCR) that yield in PCR products of distinguishable size (Table 3) using 10 ng of mouse genomic DNA from NIH 3T3 cells as template. The PCR cycling protocol consists of an initial denaturation/hot-start polymerase activation step [15 min 95° C. for HotStarTaq (QIAGEN), 2 min 95° C. for standard Taq polymerase (QIAGEN)] and 35 cycles (30 sec 94° C., 45 sec 61° C., 90 sec 72° C.) and a final extension step (15 min 68° C.). PCR was performed in a MJ Research PTC-200 thermocycler.

All reactions were performed in a final volume of 50 µl. Duplicate reactions were carried out in a reaction buffer containing Tris-HCl, pH 8.7, potassium chloride, ammonium sulphate, magnesium chloride, each dNTP, 2.5 U of the indicated heat-stable DNA polymerase and 0.2 µM of each of the forward and reverse primers given in Table 1. Additionally, different concentrations of volume excluding reagent were added to the reactions.

Reactions in Example 1 additionally contained 0, 1, 3 or 6 wt-% of Dextran with average MW 35.000-45.000 Dalton as indicated. Reactions in Example 2 contained 0, 1, 3 or 6 wt-% of PEG-8000.

An aliquot (10 µl) of each reaction was analysed on a 1.3% agarose gel and product yield was densitometrically determined. Samples exhibiting the highest product yield were set to 100%.

Example 3

The effect of the combination of a hot-start DNA polymerase and a volume excluding reagent on multiplex PCR was studied in a reaction mixture containing 2 different sets of primers and sequence specific probes for the human genomic loci of CSBG and c-myc (see Table 5) and 10 ng or 1 ng of human genomic DNA as template. The PCR reactions were done using the QuantiTect Probe PCR Kit (QIAGEN) contained 0 (standard), 1, 3 or 6 wt-% of PEG-8000. Example 1 and 2 clearly showed that the use of a non-hot-start method using standard Taq is not feasable in Multiplex PCR and experiments in this example were done using a hot start polymerase.

The PCR cycling protocol consists of an initial denaturation/hot-start polymerase activation step [15 min 95° C. for hot-start polymerase HotStarTaq™ included in the QuantiTect Probe PCR Master Mix] and 40 cycles (30 sec 94° C. denaturation, 60 sec 60° C. combined annealing/extension step).

Multiplex PCR was done as real-Time multiplex PCR in a final volume of 20 µl using a 7900HT Sequence Detection System (Applied Biosystems) and the 384 well block module and fluorescence data were collected during the reaction.

The sequence specific probes used in this example are cleaved by the 5'-3' exonuclease activity of the HotStarTaq™ upon hybridisation to its target sequence in each PCR cycle. The use of the present invention is not limited to this probe type. The use of other types of sequence specific probes compatible to real-time PCR known in the art like Hybridisation Probes (FRET-Probes), Molecular Beacons, Scorpions or upcoming new probe technologies are also possible embodiments.

Cleavage of the probe by the 5'-3' exonuclease activity leads to a separation of the fluorescent dye and the quencher molecule which leads to an increase in fluorescence intensity of the fluorescent dye attached to the 5' end of the probe. Amplification of each of the PCR products can be followed after PCR by changes in the fluorescence signal of the respective dye. The software supplied with the 7900HT was used to generate curves showing the changes in fluorescence versus the PCR cycle number, referred to as amplification plots. A threshold cycle (Ct) was defined for each of the two fluorophores using the software. Passive reference dye was set to "none" for data analysis.

The Ct value is a measurement for the efficiency of the PCR reaction and number of starting template molecules. When comparing different experimental conditions, improvements of the experimental conditions result in lowered Ct values. Results of example 3 are summarized in Table 5.

In this table 5, threshold cycle numbers (Ct values) of the experiments described in example 3 are shown of samples amplified in presence or absence of PEG-8000. Mean Ct values of triplicates and coefficient of variation is given.

TABLE 5

| | HotStarTaq | | | | | | | |
|---|---|---|---|---|---|---|---|---|
| | PEG-8000 [wt-%] | | | | | | | |
| | 0% | | 1% | | 3% | | 6% | |
| PCR System | Mean Ct | Cv | Mean Ct | Cv | Mean Ct | Cv | Mean Ct | Cv |
| CSBG 10 ng template | 32.69 | 0.97 | 31.05 | 0.97 | 29.88 | 0.29 | 30.18 | 3.42 |
| c-myc 10 ng Template | 27.25 | 0.53 | 27.34 | 0.14 | 27.62 | 0.15 | 27.90 | 1.22 |
| CSBG 1 ng Template | 36.50 | 1.15 | 35.24 | 0.29 | 33.48 | 1.02 | 33.70 | 1.60 |
| c-myc 1 ng Template | 30.67 | 0.40 | 30.69 | 0.79 | 30.81 | 0.09 | 30.67 | 1.08 |

Mean Ct: mean Ct of triplicate reactions
Cv: coefficient of variation

The invention claimed is:

1. A method for coamplification of two or more target nucleic acids having different sequence compositions present at comparable copy numbers wherein the maximum difference between the lowest and highest copy number is 10-fold said method comprising at least 15 primary amplification cycles, each amplification cycle comprising the sequential steps of:

(A) heating a reaction mixture of two or more target nucleic acids, or their primer extension products, at a first temperature, $T_1$, for denaturation of the strands of the target nucleic acids or their primer extension products, and (B) priming the denatured strands with a set of primers specific to and hybridizable with opposing strands of each target nucleic acid to be amplified, by cooling to a second temperature, $T_2$, and (C) either as a continuation of step (B) or in a separate step, forming primer extension products in a reaction mixture of PCR reagents, by incubation at a third temperature, $T_3$, provided that when priming and primer extension product formation are carried out in the same step, $T_2$ and $T_3$ are the same, and wherein the reaction mixture in at least one of the primary amplification cycles comprises from 1 to 20 weight % of a nonionic, polymeric volume exclusion agent, a thermostable hot start DNA polymerase, and optionally a sequence specific labeled probe which binds with the primer binding regions and which is detectable after hybridization, and

(D) in the course of the reaction in each amplification cycle or in an amplification cycle after the last primary amplification cycle detecting one or more of the primer extension products as an indication of one or more of the target nucleic acids.

2. The method for coamplification of two or more target nucleic acids having different sequence compositions according to claim 1, wherein the amount of nonionic polymeric volume exclusion agent in said reaction mixture is 1 to 15 weight %.

3. The method for coamplification of two or more target nucleic acids having different sequence compositions according to claim 1, wherein the amount of nonionic polymeric volume exclusion agent in said reaction mixture is 1 to 8 weight %.

4. The method according to one of claim 1, 2, or 3, wherein the volume exclusion agent is selected from the group consisting of a polyether, a reaction product of a sugar with epichlorohydrin, a polysaccharide, and a polyacrylate.

5. The method according to claim 4, wherein the volume exclusion agent is selected from the group of polyethers of the general formula:

wherein R is an alkylene bridge of 1 to 6 carbon atoms—branched or unbranched—and n is an integer of 15 to 1000.

6. The method according to claim 5, wherein R may represent 1,2-ethylene, 1,3-propylene, 1,2-propylene, 2-hydroxy-1,3-propylene, 3-hydroxy-1,2-propylene, 1,4-butylene, 1,3-butylene, or 1,2-hexylene.

7. The method according to claim 5, wherein the polyether is poly(ethylene glycol).

8. The method according to claim 7, wherein the poly(ethylene glycol) has a molecular weight in the range of 1000 to 2,000,000 daltons.

9. The method according to claim 7, wherein the poly(ethylene glycol) has a molecular weight in the range of 3000 to 500,000 daltons.

10. The method according to claim 7, wherein the poly(ethylene glycol) has a molecular weight of about 8000 daltons.

11. The method according to claim 4, wherein the volume exclusion reagent is a dextran.

12. The method according to claim 11, wherein the dextran has a molecular weight in the range of 1000 to 2,000,000 daltons.

13. The method according to claim 11, wherein the dextran has a molecular weight in the range of 3000 to 500,000 daltons.

14. The method according to claim 11, wherein the dextran has a molecular weight in the range of 40,000 to 60,000 daltons.

15. The method according to claim 4, wherein the polyacrylate is selected from the group consisting of poly(hydroxyethyl acrylate) or poly(2,3-dihydroxypropyl acrylate).

16. The method according to any one of claim 1, 2, or 3 wherein said chemically thermostable hot start DNA polymerase is modified by reaction with an aldehyde.

17. The method according to claim 1, wherein one of the primers of each primer set is fluorescently labeled.

18. The method according to claim 1, wherein one of the primers of each primer set is labeled with a specific binding moiety.

19. The method according to claim 1, wherein the sequence specific labeled probe is fluorescently labeled.

20. The method according to claim 1 wherein each set of primers hybridizable with opposing strands of each target nucleic acid to be amplified is different.

21. The method according to claim 1 wherein the method is capable of coamplifying six (6) different target nucleic acids.

22. The method according to claim 1 wherein the method is capable of coamplifying eight (8) different target nucleic acids.

23. The method according to claim 1 comprising six (6) different target nucleic acids.

24. The method according to claim 1 comprising eight (8) different target nucleic acids.

25. The method according to claim 1 comprising eight (8) sets of primers.

26. The method according to claim 1 comprising seven (7) different target nucleic acids.

27. The method according to claim 1 wherein the sets of primers are present in equimolar primer concentrations.

28. The method according to claim 1 wherein a set of primers is present in a concentration that makes it a rate limiting reactant.

* * * * *